United States Patent [19]
Antonine et al.

[11] Patent Number: 5,451,872
[45] Date of Patent: Sep. 19, 1995

[54] DETECTION DEVICE FOR DETECTING LONGITUDINAL CRACKS ON SLABS ISSUING FORM A CONTINUOUS CASTING

[75] Inventors: Claude Antonine, Sausset-les-Pins; Martine Depeyris, Marseille, both of France

[73] Assignee: Sollac, Puteaux, France

[21] Appl. No.: 66,008

[22] PCT Filed: Nov. 27, 1991

[86] PCT No.: PCT/FR91/00942
§ 371 Date: Sep. 8, 1993
§ 102(e) Date: Sep. 8, 1993

[87] PCT Pub. No.: WO92/09887
PCT Pub. Date: Jun. 11, 1992

[30] Foreign Application Priority Data
Nov. 29, 1990 [FR] France .................................. 90 14953

[51] Int. Cl.⁶ ...................... G01N 27/90; B22D 11/12
[52] U.S. Cl. ...................................... 324/262; 324/225; 324/238; 324/242; 164/451
[58] Field of Search ............... 324/225, 226, 227, 229, 324/232, 238, 240, 242, 262; 164/451

[56] References Cited

U.S. PATENT DOCUMENTS

| | | | |
|---|---|---|---|
| 2,537,731 | 1/1951 | Angell | 324/229 |
| 4,534,405 | 8/1985 | Hulek et al. | 324/228 X |
| 4,855,678 | 8/1989 | Kreiskorte | 324/262 |

FOREIGN PATENT DOCUMENTS

| | | | |
|---|---|---|---|
| 0088069 | 9/1983 | European Pat. Off. | |
| 0390009 | 10/1990 | European Pat. Off. | |
| 2121544 | 12/1983 | United Kingdom | 324/262 |

*Primary Examiner*—Gerard R. Strecker
*Attorney, Agent, or Firm*—Oblon, Spivak, McClelland, Maier & Neustadt

[57] ABSTRACT

A device for detecting longitudinal cracks on slabs, in particular on steel slabs, issuing from a continuous casting, by way of eddy current measuring probes fed with an alternating voltage, and device for detecting variations in the voltage indicating the presence of a crack. The device for detecting longitudinal cracks includes on each side of upper and lower faces of the slab, a crack detection unit each including a measuring probe which undergoes a transverse reciprocating motion relative to the direction of travel of the slab, and a device for maintaining the measuring probe of each detection unit at a constant distance relative to the corresponding main face of the slab.

11 Claims, 4 Drawing Sheets

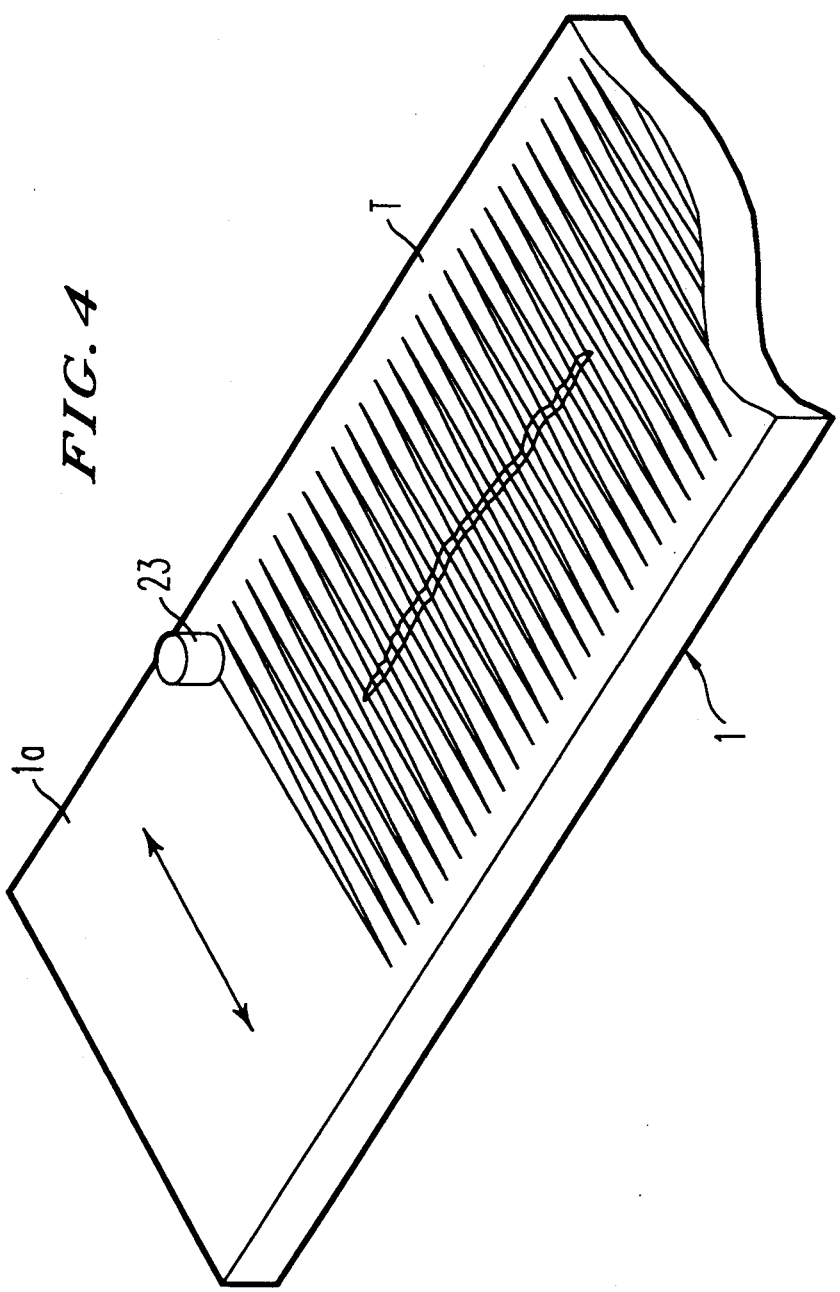

DETECTION DEVICE FOR DETECTING LONGITUDINAL CRACKS ON SLABS ISSUING FORM A CONTINUOUS CASTING

BACKGROUND OF THE INVENTION

1 Field of the Invention

The present invention relates to a device for detecting longitudinal cracks on slabs, in particular on steel slabs issuing from a continuous casting.

2. Discussion of the Background

It is known that continuous casting creates difficulties due to the appearance of surface defects or cracks on the faces of the slabs. These defects must be absolutely repaired before the slabs are drawn and rolled.

The solution consisting in systematically retreating all the slabs is too expensive and it is therefore necessary to detect the cracks on the slabs at the output end of the continuous casting so as to deviate to a subsequent retreatment solely the slabs which have cracks requiring said treatment.

These cracks extend longitudinally relative to the axis of the slab and may be located just as well on the lateral faces as on the main faces of the slab.

A device for detecting cracks on slabs by means of eddy current probes is known and comprises an induction coil fed with alternating voltage and means for detecting variations in said voltage indicating the presence of a crack.

This device comprises on each side of the passage of the slabs a vertical probe maintained in proximity to an edge, and a plurality of horizontal probes located at different levels and maintained in proximity to a lateral face of the slab.

The presence of a crack substantially modifies the impedance of the induction coil and the eddy currents and results in a variation in the amplitude of the voltage exciting the coil and in the phase shift between the voltage and the current exciting said coil.

The analysis of the excitation voltage of the coil by electronic circuits provides an electric signal which presents amplitude peaks in the presence of a crack.

But this device detects solely cracks located on the narrow faces of the slabs and does not permit detecting the presence of longitudinal cracks on the main faces of the slabs

SUMMARY OF THE INVENTION

An object of the invention is to provide a device for detecting longitudinal cracks on the main faces of a hot slab issuing from a continuous casting for the purpose of deviating the slabs toward a subsequent retreatment.

This is achieved in employing a detection device which comprises eddy current measuring probes and is so designed that, irrespective of the deformations of the slab and the roughness of its surface, the end of said probes are spaced away from the surface of the slab by a very small constant distance without this resulting in an excessive wear of these probes which must be capable of resisting wear and abrasion throughout the continuous casting procedure so that the wear of the probes does not require stoppage of the continuous casting.

The measuring probes must be held and guided at the short distance from the surface of the slabs without interposing between the end of the coil and said surface any metal part which would disturb the magnetic circuit.

The width of the air gap must remain constant whatever the shape and roughness of the surface to be checked, since very slight variations in the width of the air gap would result in variations in the coefficient of mutual induction which could result in variations in the electric signal having amplitudes of the same order as the variations due to the cracks, with the risk of deviating slabs exempt from defects by error.

The necessity to maintain an air gap of constant width between the measuring probe and the surface of the slab requires mounting the measuring probes on movable supports which must faithfully follow all the sinuosities of the surface and which temporarily move away from the slab in front of asperities having a steep leading edge.

The present invention permits attaining these objects and provides a device for detecting longitudinal cracks on slabs, in particular on steel slabs, issuing from a continuous casting, by means of measuring probes employing eddy currents fed with alternating voltage, and means for detecting variations in said voltage indicating the presence of a crack, comprising on each side of the main faces of the slab, a crack detecting unit each carrying a measuring probe which undergoes transverse alternating motion with respect to the direction of travel of the slab, characterized in that the device further comprises means for maintaining the measuring probe of each detection unit at a constant distance from the corresponding main face of the slab.

According to other features of the invention:

each detection unit comprises means for adjusting the position of the measuring probe as a function of the surface state of the corresponding main face of the slab, each detection unit comprises an arm perpendicular to the direction of travel of the slab and extending throughout the width of said slab, the arm of the first detection unit being disposed above the upper main face of the slab and the arm of the second detection unit being disposed under the lower main face of said slab, each arm is mounted to be movable in a direction perpendicular to the main faces of the slab on a frame which is movable in a direction perpendicular to the direction of travel of the slab for bringing said arms on each side of the main faces of said slab, each arm is connected to the frame by links forming an articulated parallelogram structure, the measuring probe of each detection unit is driven transversely relative to the direction of travel of the slab by a shaft of a traversing unit, said shaft being disposed longitudinally in the corresponding arm of said detection unit and said traversing unit comprising a constant-speed motor driving the shaft in rotation through a transmission box reversing the direction of rotation of said shaft, the means for maintaining each measuring probe at a constant distance from the corresponding main face of the slab comprise a single-acting jack interconnecting the two arms of the detection units and exerting a continuous traction on said arms, and an abutment means mounted on each arm and adapted to come into contact with the corresponding main face of the slab, the means for adjusting the position of each measuring probe comprise a sensor mounted on the corresponding arm of the detection unit and disposed in confronting relation to the main face of the slab, and an electromechanical counter-thrust jack controlled by said sensor, said sensor is fixed and consists of an eddy current probe, the electromechanical counter-thrust jack comprises a fixed part fixed to the frame and a movable part connected to and acting on the arm of the detection unit comprising the sensor controlling said jack, the measuring probe disposed above the upper main face is associated with two detectors of asperities on said main face and each disposed on each side of said measuring probe with respect to the direction of travel of said probe, each detector controls through a single-acting jack the opening of the arms of the detection units, the arm disposed above the upper main face of the slab includes a counterweight at its end close to the frame.

BRIEF DESCRIPTION OF THE DRAWINGS

Further features and advantages of the invention will be apparent from the following description, with reference to the accompanying drawings which are given solely by way of example and in which:

FIG. 4 is a diagrammatic perspective view showing the path of a measuring probe on the upper main face of a slab.

DESCRIPTION OF THE PREFERRED EMBODIMENT

Figure 1:
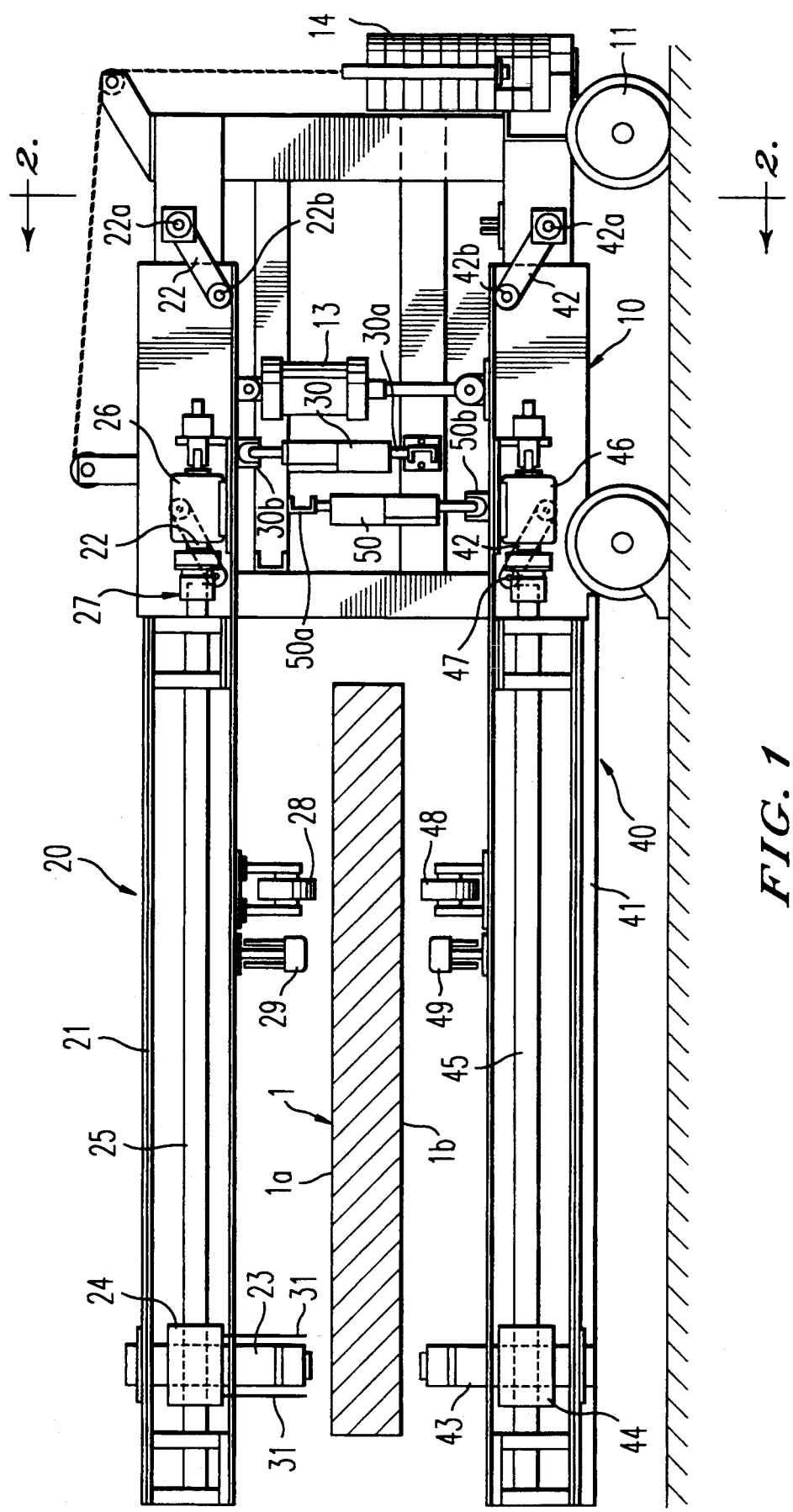
FIG. 1 is a diagrammatic assembly view of a detection device according to the invention, the detection units being in positions moved away from the slab.
Figure 2:
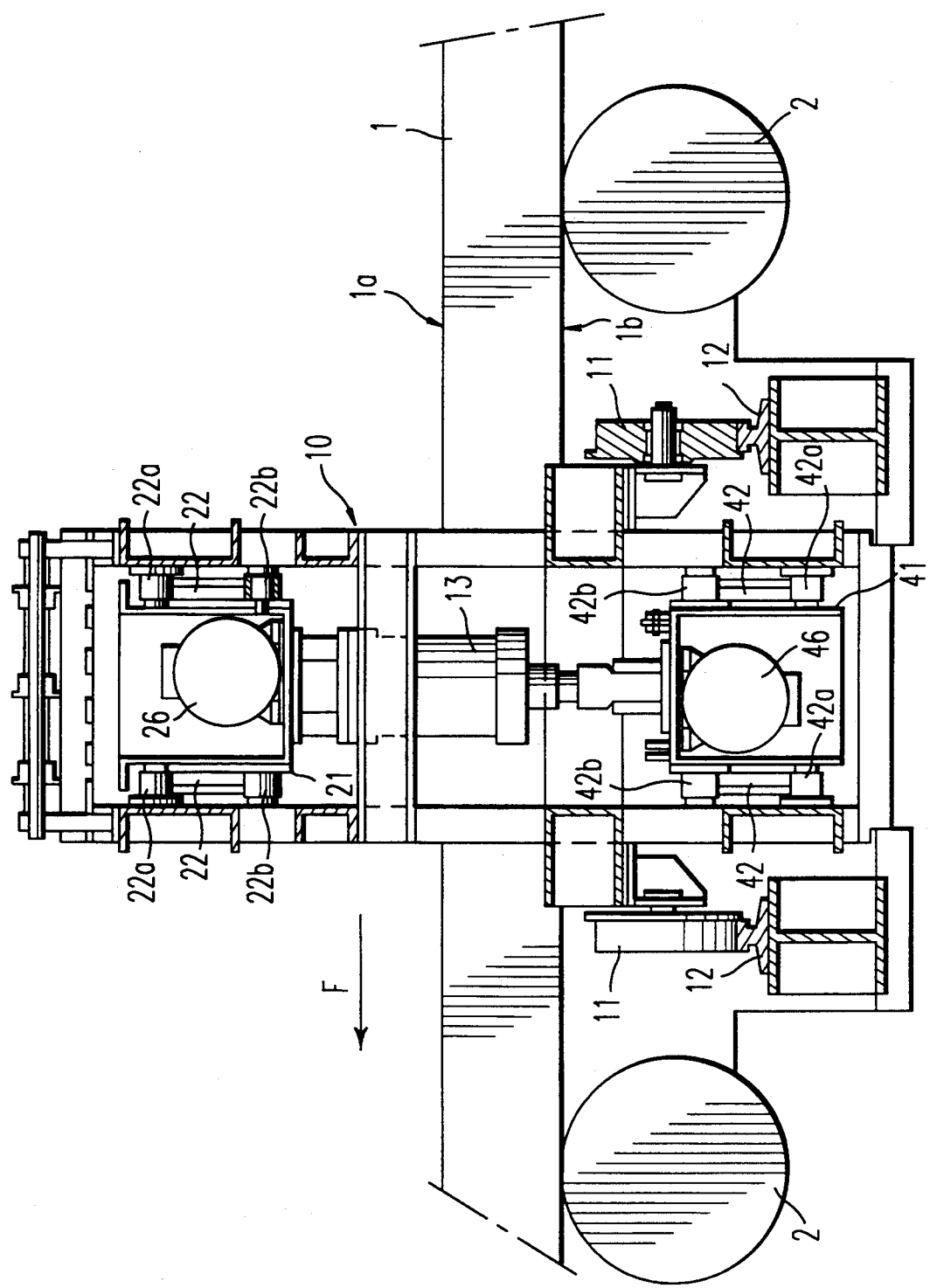
FIG. 2 is a sectional view taken on line 2—2 of FIG. 1.
Figure 3:
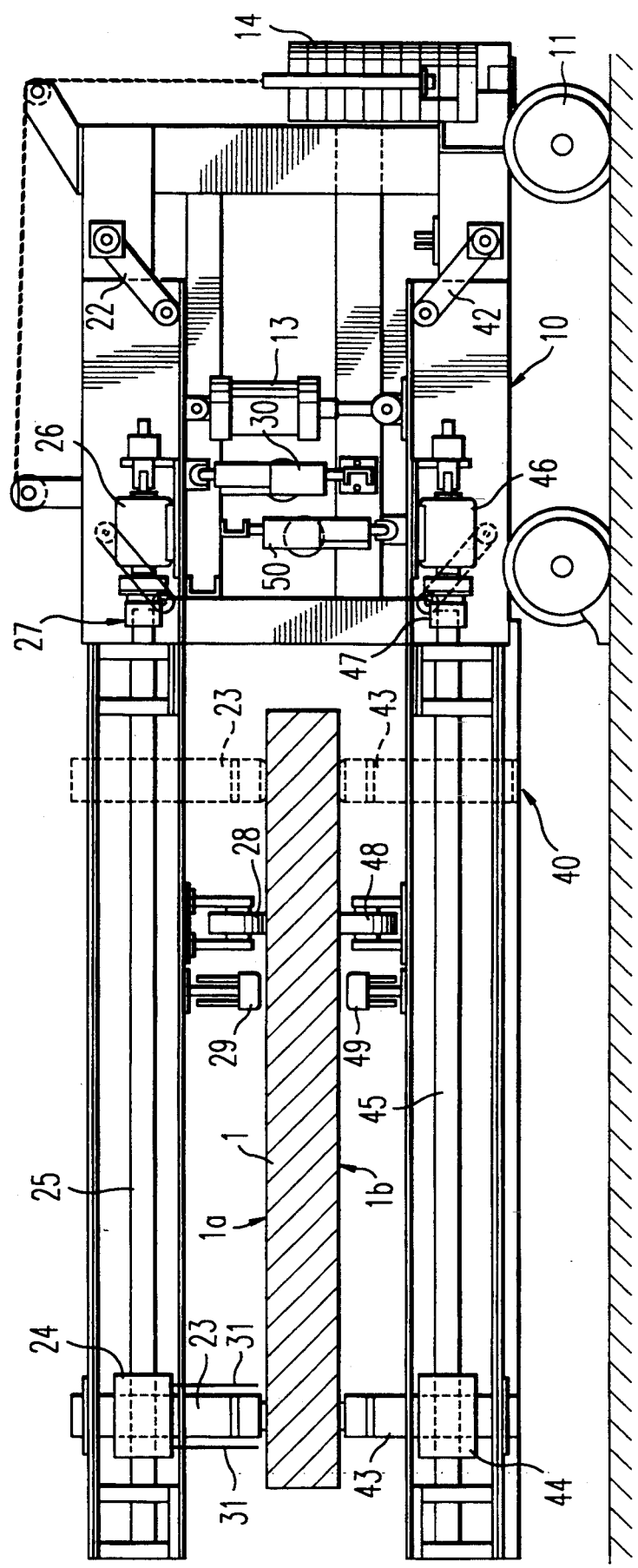
FIG. 3 is a view identical to FIG. 1 with the detection units in a position close to the slab for the detection of longitudinal cracks.

FIGS. 1 to 3 show a slab 1, in particular of steel, issuing from a continuous casting and travelling along rollers 2.

An example of the direction of travel of the slab is illustrated by the arrow F (FIG. 2). This slab 1 has a substantially rectangular sectional shape.

The detection device according to the invention detects the longitudinal cracks simultaneously on the main faces 1a and 1b of the slab 1.

This detection device shown in FIGS. 1 to 3 comprises a frame 10 mounted to be movable in a direction perpendicular to the direction of travel of the slab 1 on wheels 11 which roll along rails 12.

The device comprises two identical detection units 20 and 40 respectively, an upper detection unit 20 extending above the upper face 1a of the slab 1 and a lower detection unit 40 extending under the lower face 1b of the slab 1.

The upper detection unit 20 comprises an arm 21 perpendicular to the direction of travel of the slab 1 and extending throughout the width of the latter when the device is in operation.

The arm 21 is mounted to be movable in a direction perpendicular to the main faces 1a and 1b of the slab 1 on the frame 10 by means of four links 22 forming an articulated parallelogram structure (FIG. 2).

Each link 22 has an end 22a articulated to the frame 10 and an opposite end 22b articulated to the arm 21.

The upper arm 21 carries a measuring probe 23 which undergoes a transverse reciprocating motion relative to the direction of travel of the slab 1, this probe extending toward the main face 1a of the slab.

To this end, the measuring probe 23 is carried by a collar 24 mounted on a shaft 25 of a traversing unit, said shaft being disposed longitudinally in the arm 21. This traversing unit further comprises a constant-speed motor 26 for driving the shaft 25 in rotation through a transmission box 27 which reverses the direction of rotation of said shaft so as to impart to the measuring probe 23 a reciprocating motion relative to the main face 1a of the slab 1.

Likewise, the lower detection unit comprises an arm 41 perpendicular to the direction of travel of the slab 1 and extending throughout the width of the latter.

The arm 41 is mounted to be movable in a direction perpendicular to the main faces 1a and 1b of the slab 1 on the frame 10 by means of four links 42 forming an articulated parallelogram structure (FIG. 2).

Each link 42 has an end 42a articulated to the frame 10 and an opposite end 42b articulated to the arm 41.

The lower arm 41 carries a measuring probe 43 which undergoes a transverse reciprocating motion relative to the direction of travel of the slab 1 and extends toward the main face 1b of the latter.

The measuring probe 43 is carried by a collar 44 mounted on a shaft 45 of a traversing unit, said shaft being disposed longitudinally in the arm 41.

This traversing unit further comprises a constant speed motor 46 for driving the shaft 45 in rotation through a transmission box 42 which reverses the direction of rotation of said shaft so as to impart to the measuring probe 43 a to and fro motion relative to the lower main face 1b of the slab 1.

Further, the detection device comprises means for maintaining the measuring probes 23 and 43 at a constant distance from the respective main faces 2a and 1b of the slab 1.

These means are formed by a single-acting jack 13 and two abutment means 28 and 48 respectively, one abutment means 28 being carried by the arm 21 and adapted to come into contact with the upper main face 1a and the other abutment means 48 being carried by the arm 41 and adapted to come into contact with the lower main face 1b.

The single-acting jack 13 is disposed transversely relative to the arms 21 and 41 and interconnects these two arms. This jack 13 is maintained constantly under pressure and exerts a continuous traction on the arms 21 and 41.

The abutment means 28 and 48 are constituted for example by rollers.

Each detection unit 20 and 40 comprises means for adjusting the position of the measuring probes 23 and 43 as a function of the surface state of the main faces 1a and 1b of the slab.

As concerns the detection unit 20, these means comprise, on one hand, a fixed sensor 29, for example of the type employing eddy currents, mounted on the arm 21 and disposed in confronting relation to the upper main face 1a and, on the other hand, an electromechanical counter-thrust jack 30 controlled by the sensor 29.

The counter-thrust jack 30 comprises a fixed part 30a fixed to the frame 10 and a movable part 30b connected to and acting on the arm 21 in opposition to the traction exerted by the jack 13.

The same arrangement is adopted for the detection unit 40 which comprises, on one hand, a fixed sensor 49, for example of the type employing eddy currents, mounted on the arm 41 and disposed in confronting relation to the lower main face 1b and, on the other hand, an electromechanical counter-thrust jack 50 controlled by the sensor 49.

The counter-thrust jack 50 comprises a fixed part 50a fixed to the frame 10 and a movable part 50b connected to and acting on the arm 41 in opposition to the traction exerted by the jack 13.

The measuring probe 23 is associated with two detectors 31 of asperities on the main face 1a of the slab 1, each being disposed on each side of said measuring probe 23 relative to the direction of travel of the latter.

The two detectors 31 are operationally connected to the single-acting jack 13 and are displaced at the same time as the measuring probe 23 and are each constituted for example by a balance bar which, at the moment it encounters an asperity, brings about through the single-acting jack 13, the opening of the arms 21 and 41 of the detection units 20 and 40.

The end of the arm 21 close to the frame 10 is connected to a counterweight 14 to ensure a simultaneous opening of the two arms 21 and 41.

The detection device operates in the following manner:

First of all, the arms 21 and 41 are open, the arm 21 under the effect of the counterweight 14 and the arm 41 under the effect of its own weight.

The frame 10 is moved along the rails 12 in such manner as to position the arms 21 and 41 on each side of the passage of the slab 1 as shown in FIG. 1.

The jack 13 is actuated and this causes the closure of the arms 21 and 41, the abutment means 28 and 48 corning into contact with the respective main faces 1a and 1b of the slab.

The jack 13 exerts a continuous traction on the arms 21 and 41 so as to maintain the measuring probes 23 and 43 at about 2 mm from the main faces of the slab (FIG. 3).

These measuring probes 23 and 43 undergo a reciprocating motion relative to the direction of travel of the slab 1 owing to the action of the shafts 25 and 45, the motors 26 and 46 and the transmission boxes 27 and 47.

The measuring probes 23 and 43 sweep over the main faces 1a and 1b at a speed of about one meter per second and the slab 1 travels at about 1.4 meter per minute.

Consequently, the path T of the measuring probe 23 on the main face 1a has a sinusoidal shape (FIG. 4).

The same is true of the path of the measuring probe 43 on the main face 1b.

The presence of a crack substantially modifies the impedance of the induction coil and the eddy currents and results in a variation in the amplitude of the excitation voltage of the measuring probes.

The analysis of the excitation voltage by electronic circuits provides an electric signal which presents, in the presence of a crack, amplitude peaks therefore providing a crack detection signal.

The sensor 29 adjusts the position of the measuring probe 23 as a function of the longitudinal undulations of the upper face 1a by controlling the counter-thrust jack 30 which vertically shifts the arm 21 against the traction exerted by the jack 13.

The sensor 49 adjusts the position of the probe 43 as a function of the longitudinal undulations of the lower face 1b by controlling the counter-thrust jack 50 which vertically shifts the arm 41 against the traction exerted by the jack 13.

If in the course of the reciprocating motion of the measuring probe 23 one of the detectors 31 encounters an asperity having a height exceeding 1.5 mm on the main face 1a, this detector immediately brings about the opening of the arms 21 and 41 by means of the jack 13 and this avoids any deterioration of the measuring probes.

The measuring probes are maintained at a constant distance from the main faces of the slab, this short distance being necessary for high sensitivity with respect to the cracks.

Further, the measuring probes are cooled and maintained at a temperature of the order of 20° C. notwithstanding the proximity of the slab whose temperature exceeds 300° C.

The detection device according to the invention therefore permits simultaneously detecting the longitudinal cracks on the two main faces of the slab for different slab widths.

We claim:

1. A device for detecting longitudinal cracks on slabs which issue from a continuous casting, the device comprising:

a frame;

first and second crack detection units mounted on said frame through links which form an articulated parallelogram structure and extend through a width of said slab, wherein each of said first and second crack detection units is formed by an arm which is perpendicular to a direction of travel of the slab, such that said first crack detection unit extends over an upper face of said slab, and said second crack detection unit extends under a lower face of said slab;

first and second measuring probes respectively mounted on said first and second crack detection units, said measuring probes being fed with an alternating voltage and employing eddy currents;

means for detecting variations in said alternating voltage which is indicative of a crack in said slab;

first and second means for respectively transversely reciprocating each of said first and second measuring probes relative to the direction of travel of the slab, said first and second reciprocating means being mounted on each of the first and second crack detention units; and means for maintaining each of the first and second measuring probes at a constant distance from a corresponding upper and lower face of the slab, said maintaining means being coupled to each of the first and second crack detection units.

2. A device according to claim 1, wherein each of said detection units comprises means for adjusting a position of each of said measuring probes in response to said means for detecting voltage variations, wherein the position of each of said measuring probes is a function of a surface state of the corresponding face of the slab.

3. A device according to claim 2, wherein the means for adjusting the position of each measuring probe comprise a sensor mounted on the corresponding arm of the detection unit and disposed in confronting relation to the main face of the slab, and an electromechanical counter-thrust jack controlled by said sensor.

4. A device according to claim 3, wherein said sensor is fixed and is formed by an eddy current probe.

5. A device according to claim 3, wherein the counter-thrust jack comprises a fixed part fixed to the frame and a movable part connected to and acting on the arm of the detection unit comprising the sensor controlling said jack.

6. A device according to claim 1, wherein the first and second means for transversely reciprocating each of the measuring probes relative to the direction of travel of the slab comprises a shaft of a traversing unit, said shaft being disposed longitudinally in the corresponding arm of said detection unit, said traversing unit comprising a constant-speed motor for driving the shaft in rotation through a transmission box for reversing the direction of rotation of said shaft.

7. A device according to claim 1, wherein the means for maintaining each measuring probe at a constant distance from the corresponding upper and lower face of the slab comprise a single-acting jack interconnecting the arms of the detection units and exerting a continuous traction on said arms, and an abutment means mounted on each arm and adapted to come into contact with the corresponding main face of the slab.

8. A device according to claim 1, further comprising two detectors of asperities on said faces of said slab, each of the detectors being positioned on each side of said measuring probe disposed above the upper face of said slab relative to a direction of displacement of the measuring probe.

9. A device according to claim 8, wherein each detector of asperities controls through the single-acting jack the opening of the arms of the detection units.

10. Device according to claim 1, wherein the arm disposed above the upper face of the slab comprises a counterweight at its end close to the frame.

11. A device according to claim 1, wherein:
each arm of said first and second detection units is mounted to said frame through said links so as to be movable in a direction perpendicular to the upper and lower faces of the slab, and said frame is movable in the direction perpendicular to the direction of travel of said slab so as to permit the arms to be positioned above and below said upper and lower faces of said slab.

* * * * *